US006156557A

United States Patent [19]

Moriyama et al.

[11] Patent Number: 6,156,557
[45] Date of Patent: Dec. 5, 2000

[54] ALKALINE PROTEASE FROM STREPTOMYCES SP. AND METHOD FOR PREPARING THE SAME

[75] Inventors: Yasushi Moriyama; Shinji Mitsuiki, both of Kita-kyushu, Japan

[73] Assignee: Toto Ltd., Kita-kyushu, Japan

[21] Appl. No.: 09/076,842

[22] Filed: May 13, 1998

[51] Int. Cl.[7] ............................. C12N 9/58; C12N 9/52; D06M 16/00; C11D 7/42; C12S 9/00
[52] U.S. Cl. ..................... 435/223; 435/220; 435/264; 510/392
[58] Field of Search ..................... 435/220, 223, 435/264; 510/392

[56] References Cited

FOREIGN PATENT DOCUMENTS

09/21855  5/1997  Japan .

*Primary Examiner*—Jon P. Weber
*Attorney, Agent, or Firm*—Burns, Doane, Swecker & Mathis, LLP

[57] ABSTRACT

Disclosed is an alkaline protease having a specific activity of 214,000 (U/mg protein) when using casein as a substrate and 52,700 (U/mg protein) when using keratin as a substrate. The alkaline protease is produced by a strain belonging to alkalophilic actinomycetes, Streptomyces, particluraly Streptomyces sp. TOTO-9305 strain (FERM P-13640).

11 Claims, 4 Drawing Sheets

ALKALINE PROTEASE FROM STREPTOMYCES SP. AND METHOD FOR PREPARING THE SAME

BACKGROUND OF THE INVENTION

The present invention relates to a novel alkaline protease, a method for preparing the novel alkaline protease and a novel alkalophilic actinomycete strain having an ability of producing the alkaline protease.

The alkaline protease is an enzyme which can specifically hydrolyze the peptide bond of proteins under an alkaline condition and has widely been used in various industrial fields such as food, textile, leather and detergent industries. It has been known that such alkaline proteases are produced by a wide variety of microorganisms such as filamentous fungi, yeast and bacteria and are also produced by a group of microorganisms which belong to the so-called alkalophilic microorganisms.

As alkaline proteases produced by the foregoing alkalophilic microorganisms, there have already been known a lot of enzymes such as those produced by so-called alkalophilic Bacillus (see, for instance, Japanese Examined Patent Publication (hereinafter referred to as "J. P. KOKOKU") No. Hei 7-63366, J. P. KOKOKU Nos. Hei 7-63367 and Hei 7-63368) and these enzymes have been developed for use principally in detergents. In addition, there have also been known, for instance, an alkaline protease produced by the strain AH-101 (Japanese Un-Examined Patent Publication (hereinafter referred to as "J. P. KOKAI") No. Hei 2-255087) and an alkaline protease produced by the strain B18-1 (J. P. KOKOKU No. Hei 7-63368), as heat-stable enzymes produced by strains belonging to the genus alkalophilic Bacillus similar to the foregoing. However, there has not widely been known proteases produced by strains belonging to the alkalophilic actinomycetes which fall within the scope of alkalophilic microorganisms and there has been reported only a limited number of enzymes such as those derived from strains belonging to the genus alkalophilic Streptomyces (Agr. Biol. Chem., 1974, 38(1), pp. 37–44) and an alkaline protease produced by the strain HS682 belonging to the genus alkalophilic Thermoactinomyces (Biosci. Biotech. Biochem., 1992, 56(2), pp. 246–250).

On the other hand, when applying proteases to detergents, it has been indicated that the enzyme should act even on insoluble proteins such as keratin (M. Minagawa, SENSHO-SHI, 1985, 26, p. 322). In this case, it is needless to say that the enzyme should also intensively decompose soluble proteins such as casein. In Addition, if proteases are incorporated into detergents for bathtubs, drainage canals of bath floors and drains for dressing and washing stands, the enzymes used must maintain their activities at a moderate temperature of about 40° C. and must have an ability to intensively decompose keratin such as hairs and the dirts. The detergents and washing agents which are presently put on the market have a pH falling within an alkaline region because of their compositions and therefore, the optimum enzyme to be incorporated into these detergents and washing agents is an alkaline protease.

Moreover, hairs and feathers comprising keratin as a principal protein component are important as raw materials for preparing cysteine whose chemical synthesis is impossible. Cysteine has presently been prepared by hydrolyze hairs or the like under acidic conditions, i.e., through a chemical reaction. However, the acid-hydrolysis requires the use of severe reaction conditions and a large amount of the resulting cysteine is decomposed and this results in a quite low yield. For this reason, there has been desired for the use of mild hydrolysis such as a treatment with a protease. In this case, the enzyme as a hydrolytic agent is most preferably an alkaline protease since keratin is liable to get swollen and to be susceptible to the action of an enzyme, in a highly alkaline region.

There have been proposed the use of the alkaline protease produced by the foregoing strain AH-101 and those produced by strains belonging to the genus alkalophilic Streptomyces, for these applications. However, these enzymes are still insufficient for putting into practical use because of their low ability to decompose, in particular, keratin. Accordingly, there has been desired for the development of a novel alkaline protease possessing a higher ability to decompose proteins, in particular, keratin.

SUMMARY OF THE INVENTION

Accordingly, an object of the present invention is to provide a novel alkaline protease having a potent ability to hydrolyze insoluble proteins, in particular, keratin.

Another object of the present invention is to provide a method for preparing the foregoing novel alkaline protease.

A further object of the present invention is to provide a novel microorganism having an ability to produce the foregoing novel alkaline protease.

A still further object of the present invention is to provide a composition, such as an agent for decomposing proteins, a bath medicine, a detergent for clothings, an agent for decomposing hairs and an agent for inhibiting blockings, which comprises the novel alkaline protease as an effective component.

These and other objects of the present invention will be apparent from the following description and Examples.

The inventors of this invention have searched for microorganisms which can produce alkaline proteases having a stronger ability of keratin-decomposition while principally focusing the attention on alkalophilic actinomycetes, on the basis of the foregoing standpoint, as a result, the inventors have found out that one of actinomycetes strain belonging to the genus Streptomyces can highly efficiently produce a desired novel alkaline protease when cultivating it under aerobic culture conditions and thus have completed the present invention on the basis of the foregoing finding.

According to a first aspect of the present invention, there is provided an alkaline protease having the following enzymological properties:

(a) actions and substrate specificity: it specifically acts on a variety of proteins and peptides and thus cleaves peptide bonds thereof according to the endo-type mechanism to form low molecular weight oligopeptides and amino acids; and it is also highly active, in particular, against insoluble proteins such as keratin whose decomposition with the conventional proteases is very difficult;

(b) optimum pH: the optimum pH of the enzyme ranges from 11.0 to 11.5 when using casein as a substrate;

(c) pH range within which the enzyme is stable (stable pH range): it is stable within the pH range of from 1.5 to 12.0 when it is treated at 30° C. for 24 hours;

(d) optimum temperature: the optimum operating temperature of the enzyme ranges from 70 to 75° C.;

(e) stable temperature: the enzyme is stable up to 55° C. in the absence of calcium ions and up to 60° C. in the presence of calcium ions, when it is treated at pH 7.0 for 10 minutes;

(f) molecular weight: the enzyme has a molecular weight of about 56,000 (as determined by the SDS-polyacrylamide gel electrophoresis [SDS-PAGE] method);

(g) isoelectric point: the enzyme has an isoelectric point ranging from about 10 to 10.5 (as determined by the isoelectric focusing method);

(h) specific activity: the enzyme has a specific activity of 214,000 (U/mg protein) when using casein as a substrate and 52,700 (U/mg protein) when using keratin as a substrate; and (i) inhibition: the activity of the enzyme is not inhibited by PCMB (p-chloromercuribenzoate), iodoacetic acid and EDTA (ethylene-diaminetetraacetic acid), but is inhibited by DFP (diisopropyl fluorophosphate) and PMSF (phenyl methanesulfonyl fluoride).

According to a second aspect of the present invention, there is also provided a method for producing an alkaline protease comprising the steps of cultivating a microorganism belonging to the genus alkalophilic Streptomyces and having an ability to produce the alkaline protease having characteristic properties as specified above and isolating the resulting alkaline protease from the culture medium obtained in the foregoing step.

According to a third aspect of the present invention, there is also provided a novel strain having an ability to produce the foregoing novel alkaline protease, i.e., Streptomyces sp. TOTO-9305 strain (FERM P-13640).

According to a fourth aspect of the present invention, as use of the novel alkaline protease, there are provided various agents such as a protein decomposing agent, bathing agent, detergent, hair decomposing agent and agent for inhibiting blocking, comprising, the alkaline protease as an effective component.

BRIEF EXPLANATION OF THE DRAWINGS

The present invention will hereinafter be described in more detail with reference to the accompanying drawings, wherein.

DESCRIPTION OF THE PREFERRED EMBODIMENTS

Figure 1:
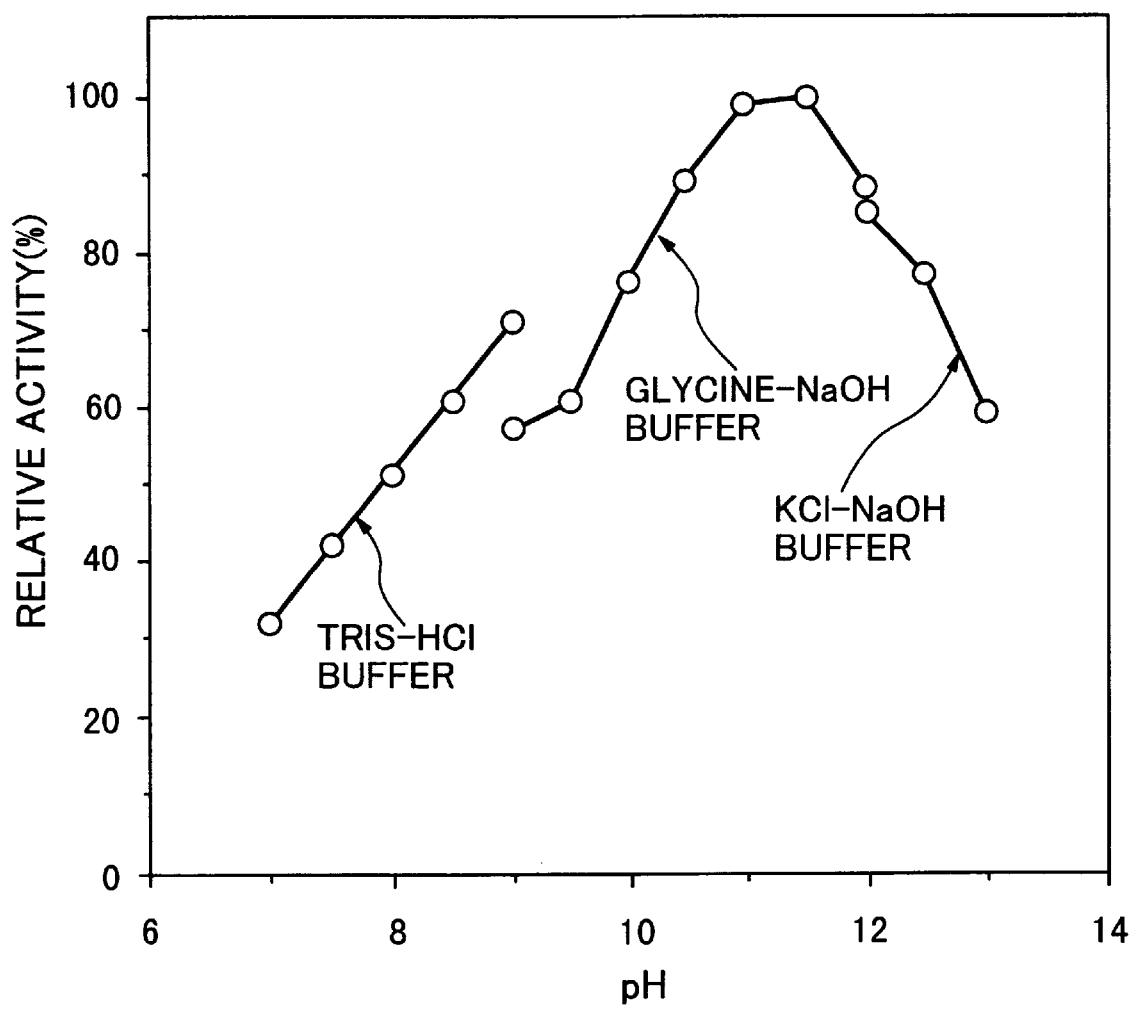
FIG. 1 is a graph showing the optimum pH of the alkaline protease of the present invention.

The alkaline protease of the present invention has a very high specific activity to decompose proteins and can effectively hydrolyze, in particular, insoluble proteins such as keratin which have not been able to be decomposed with the conventional alkaline proteases. Therefore, the novel enzyme of the present invention may ensure quite efficient effects when it is incorporated into detergents for clothings and softening agents in order to enhance the detergent action or when it is added to an anti-blocking agent (an agent for inhibiting blocking) or a detergent for bathtubs, drainage canals of bath floors and drains for dressing and washing stands. Furthermore, the enzyme of the present invention can be applied to the production of amino acids such as cysteine from, for instance, hairs and/or feathers whose principal protein constituent is keratin and thus can be used in a wide variety of industrial fields. The strain of the present invention can effectively produce the foregoing alkaline protease and extracellularly secretes the same and accordingly, the strain permits the production of the enzyme according to simple processes in a high efficiency.

Therefore, there is provided a method for decomposing insoluble protein which comprises the step of applying the protease to the insoluble protein or material containing the same. In this connection, it is preferred that the insoluble protein be keratin and the material be hair.

The present invention will further be described in more detail below.

Novel Alkaline Protease-Producing Strain

The novel alkaline protease of the present invention can be produced using a microorganism. The alkaline protease of the present invention is particularly preferably produced by a strain belonging to the genus alkalophilic Streptomyces, in particular, Streptomyces sp. TOTO-9305 strain. This strain is one isolated by the inventors of this invention from the cement joint between tiles of the domestic dwellings in Kitakyushu City, Japan. The strain is an alkalophilic actinomycete strain having microbiological properties such as those listed in the following Tables 1 and 2. In this respect, the strain is an alkalophilic microorganism and therefore, cannot grow in the usual neutral culture medium or only quite insufficiently grows therein. Accordingly, an alkaline culture medium to which 0.5% $Na_2CO_3$ is added is used in the investigations of the microbiological properties as listed in Tables 1 and 2.

TABLE 1

Microbiological Properties

| Properties | TOTO-9305 Strain |
|---|---|
| Morphology | |
| 1) Branching of spore-forming mycelia and morphology of mycelia | simple branching; straight |
| 2) Number of linked spores | not less than 10 spores (10 to 50 spores) |
| 3) Surface and size of spore | smooth; 1.0 × 0.5($\mu$m) |
| 4) Presence of flagellum | not observed |
| 5) Presence of sporangium | not observed |
| 6) Position of sporulation | on the aerial mycelia |
| Physiological Properties | |
| 1) Growth temperature range/pH | 15 to 45° C./pH 7.5 to 13 |
| 2) Gelatin-liquefaction | slightly observed (gelatin is liquefied within 4 days) |
| 3) Hydrolysis of starch | hydrolyzed |
| 4) Solidification and peptonization of skim milk | no solidification; peptonization requires 5 days |
| 5) Formation of melanin-like pigment | not formed |
| Assimilation of Carbon Sources | |
| 1) L-arabinose | + |
| 2) D-xylose | + |
| 3) D-qlucose | + |
| 4) D-fructose | + |
| 5) sucrose | + |
| 6) inositol | + |
| 7) L-rhamnose | + |
| 8) raffinose | + |
| 9) D-mannitol | + |

TABLE 2

Growth on Each Culture Medium

| Culture Medium | Growth | Color of Colony Surface | Color of substrate mycelia (surface) |
|---|---|---|---|
| Sucrose-Nitrate-Agar | good | white | colorless |
| Glucose-Asparagine-Agar | good | white | colorless |
| Glycerin-Asparagine-Agar | good | white | colorless |
| Starch-Inorganic Salt-Agar | good | white | colorless |
| Tyrosine-Agar | good | white | colorless |
| Nutrient-Agar | good | white | colorless |
| Yeast-Malt-Agar | good | white | colorless |
| Oatmeal-Agar | good | white | colorless |

| Culture Medium | Color of substrate mycelia (reverse) | Diffusible Pigment | Others |
|---|---|---|---|
| Sucrose-Nitrate-Agar | colorless | pale flesh color | |
| Glucose-Asparagine-Agar | colorless | None | |
| Glycerin-Asparagine-Agar | colorless | None | |
| Starch-Inorganic Salt-Agar | colorless | pale brown | |
| Tyrosine-Agar | colorless | pale brown | no melanin |
| Nutrient-Agar | colorless | None | |
| Yeast-Salt-Agar | colorless | None | |
| Oatmeal-Agar | colorless | pale flesh color | |

The data listed in Table 1 indicate that this strain TOTO-9305 has characteristic properties of an actinomycete strain belonging to the genus Streptomyces from the morphological standpoint. Moreover, this strain can be classified as a strain belonging to the genus Streptomyces since it has L,L-diaminopimelic acid on the cell wall.

The strain TOTO-9305 shows various bacteriological properties. For instance, it belongs to the white series because of the color tone of the colonies on a variety of agar culture mediums; the spore thereof has a smooth surface; the spore chain have an approximately straight shape; and the stain does not produce any melanin pigment. The inventors searched for species, among the known species, similar to this strain TOTO-9305 on the basis of these characteristic properties and the results of the foregoing "assimilation of various carbon sources" according to the description of Bergey's Manual of Determinative Bacteriology, 8th Ed. As a result, the inventors of this invention did not found out any species similar to the foregoing strain, in particular, in the assimilation of various carbon sources and thus have concluded that this strain is a novel one belonging to the genus Streptomyces.

In this regard, the strain TOTO-9305 has been deposited with National Institute of Bioscience and Human-Technology, Agency of Industrial Science and Technology under the accession number of 13640 (FERM P-13640).

Cultivation Conditions

The foregoing strain must be cultivated in an alkaline region since the strain is a member of alkalophilic actinomycetes. Any particular method is not necessary to make the culture medium alkaline and accordingly, it would be sufficient to simply add an alkaline agent such as sodium carbonate or sodium hydrogen carbonate to the usual culture medium. In this respect, there may be used, for instance, a variety of monosaccharides and polysaccharides such as glucose, soluble starches and celluloses as carbon sources. On the other hand, examples of nitrogen sources usable herein include inorganic substances such as nitrates and ammonium salts; urea, peptone, dry yeast, yeast extract, powdered soybean, corn steep liquor, casein, meat extract and amino acids. In addition to these carbon and nitrogen sources, the culture medium may, if necessary, comprise various kinds of inorganic salts such as magnesium, potassium and sodium salts and phosphoric acid salts. Examples of alkali sources to be added to the culture medium include carbonates such as sodium carbonate and sodium hydrogen carbonate or sodium hydroxide or ammonia and these alkali sources may be used in an amount ranging from about 0.5 to 2.0%, which is sufficient for controlling the pH value of the culture medium desirably to the range of from about 8.0 to 11.0.

The cultivation of the strain is carried out in such a culture medium at a cultivation temperature ranging from 20 to 40° C., preferably 27 to 38° C. for 2 to 5 days under aerobic conditions with stirring or shaking, if necessary.

The novel alkaline protease according to the present invention is extracellularly secreted and accumulated in the culture medium under the foregoing culture conditions.

Collection or Harvest of Enzyme

Any known purification method may be used alone or in combination in order to isolate the enzyme of the present invention from the culture medium and purify the same. This enzyme is principally secreted extracellularly (in the culture medium) and accordingly, a crude enzyme solution can easily be obtained by removing the bacterial cell of the strain through, for instance, filtration or centrifugation. The resulting crude enzyme product can be purified by any known purification methods such as salting out with, for instance, ammonium sulfate; precipitation by the addition of an organic solvent such as methanol, ethanol and/or acetone; adsorption by, for instance, keratin; ultrafiltration; gel filtration chromatography; ion-exchange chromatography; hydrophobic chromatography; and other various chromatography techniques, which may be used alone or in any combination.

A preferred purification method is as follows: First, solid ammonium sulfate is added to the filtrate of the culture medium to reach 80% saturation. After centrifugation, the resulting precipitate is collected and dissolved in a buffer solution. Thereafter, the resulting solution is applied to an ion-exchange column chromatography of CM-Toyopearl 650M (available from Tosoh Corporation) and DEAE-Toyopearl 650M (available from Tosoh Corporation) to thus obtain the purified enzyme which is uniform in SDS-PAGE.

Characteristic Properties of Enzyme

The alkaline protease of the present invention exhibits the following characteristic properties. In the following, the activity-determination method (enzyme assay) is as follows:

Activity-Determination Method: A 50 mM glycine solution in 0.5 ml of an NaCl/NaOH buffer (pH 10.5) containing 0.6% casein or 2% keratin is mixed with 0.1 ml of an enzyme solution to react them at 30° C. for 10 minutes (for 20 minutes with shaking when using keratin as a substrate), followed by addition of 2.5 ml of a trichloroacetic acid mixed solution (0.11M trichloroacetic acid, 0.22M sodium acetate, 0.33M acetic acid), allowing to stand at 30° C. for 30 minutes and filtration through filter paper No. 5C available from Advantec Company. Then 0.5 ml of the resulting filtrate is added to 2.5 ml of a 0.5M sodium carbonate solution, followed by addition of 0.5 ml of a phenol indicator diluted 3 times with stirring, allowing to stand at room temperature for 30 minutes and determination of absorbance at 660 nm. In this regard, the unit activity (1U) of the enzyme is defined to be the amount of the enzyme required for increasing the absorbance corresponding to 1 $\mu$g of tyrosine per one minute under the foregoing measurement conditions.

(1) Actions and Substrate Specificity

The enzyme acts on a protein such as casein, gelatin, gluten, hemoglobin or insulin and thus cleaves peptide bonds thereof through hydrolysis according to the endo-mechanism to form oligopeptides and amino acids. In addition, it can also strongly hydrolyze, in particular, an insoluble protein such as keratin whose decomposition with the conventional proteases is very difficult.

(2) Optimum pH and Stable pH Range

The influence of the pH on the enzyme activity was examined on the basis of the foregoing activity-determination. In this respect, there were used, as buffer solutions, KCl/HCl buffers (pH 1.0–1.5), glycine-NaCl/HCl buffers (pH 2.0–3.5), acetic acid buffers (pH 4.0–5.5), phosphoric acid buffers (pH 6.0–7.0), Tris/HCl buffers (pH 7.5–8.5), glycine-NaCl/NaOH buffers (pH 9.0–11.5) and KCl/NaOH buffers (pH 12.0–13.0). The activities of the enzyme relative to the maximum value which is assumed to be 100 are plotted on FIG. 1 as a function of pH. The results shown in FIG. 1 indicate that the optimum pH of this enzyme ranges from 11.0 to 11.5 at 30° C.

Figure 2:
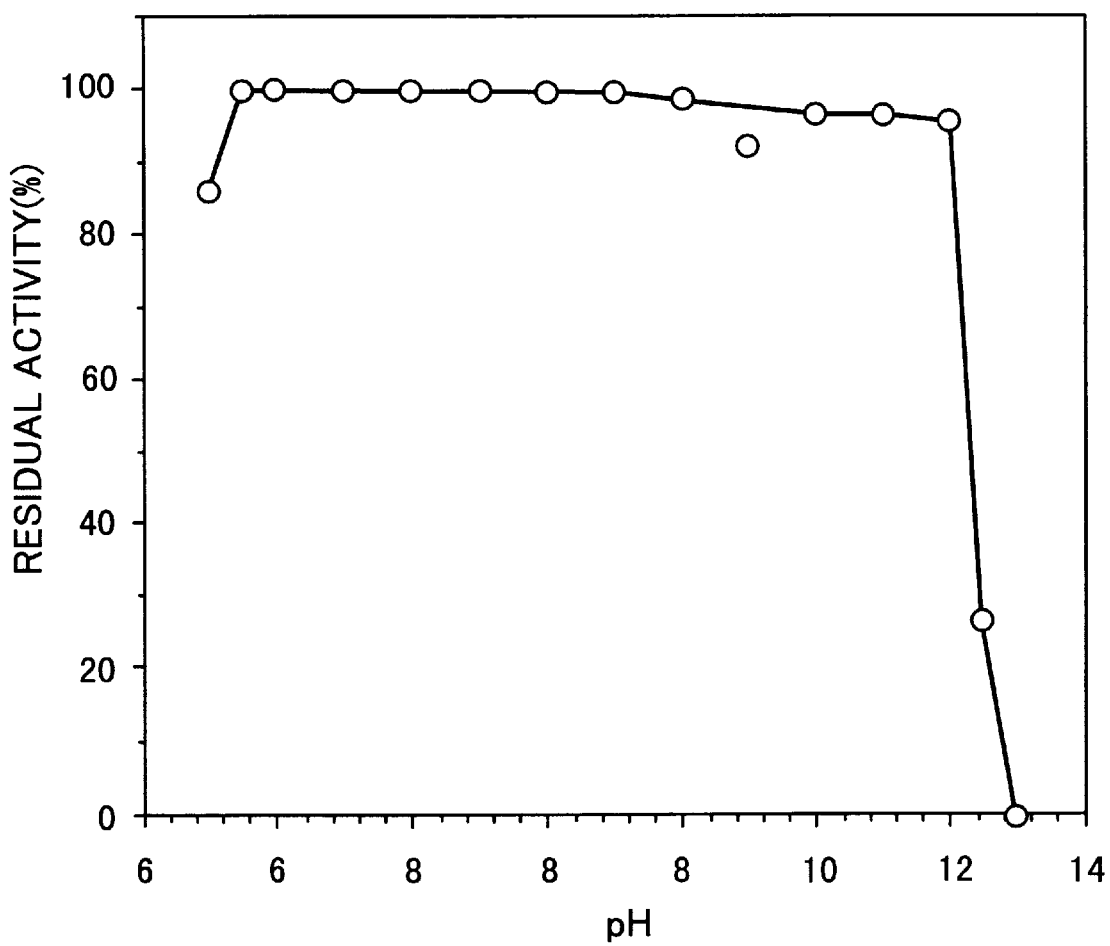
FIG. 2 is a graph showing the stable pH range of the alkaline protease of the present invention.

The stable pH range of this enzyme is likewise shown in FIG. 2. More specifically, the enzyme was maintained in a buffer solution having each pH at 30° C. for 24 hours, followed by determining the remaining activity of the enzyme relative to that of the untreated enzyme which is defined to be 100 and the results are plotted on FIG. 2. The data shown in FIG. 2 indicate that this enzyme is stable within a very wide pH range of from 1.5 to 12.0.

(3) Optimum Temperature and Stable Temperature

Figure 3:
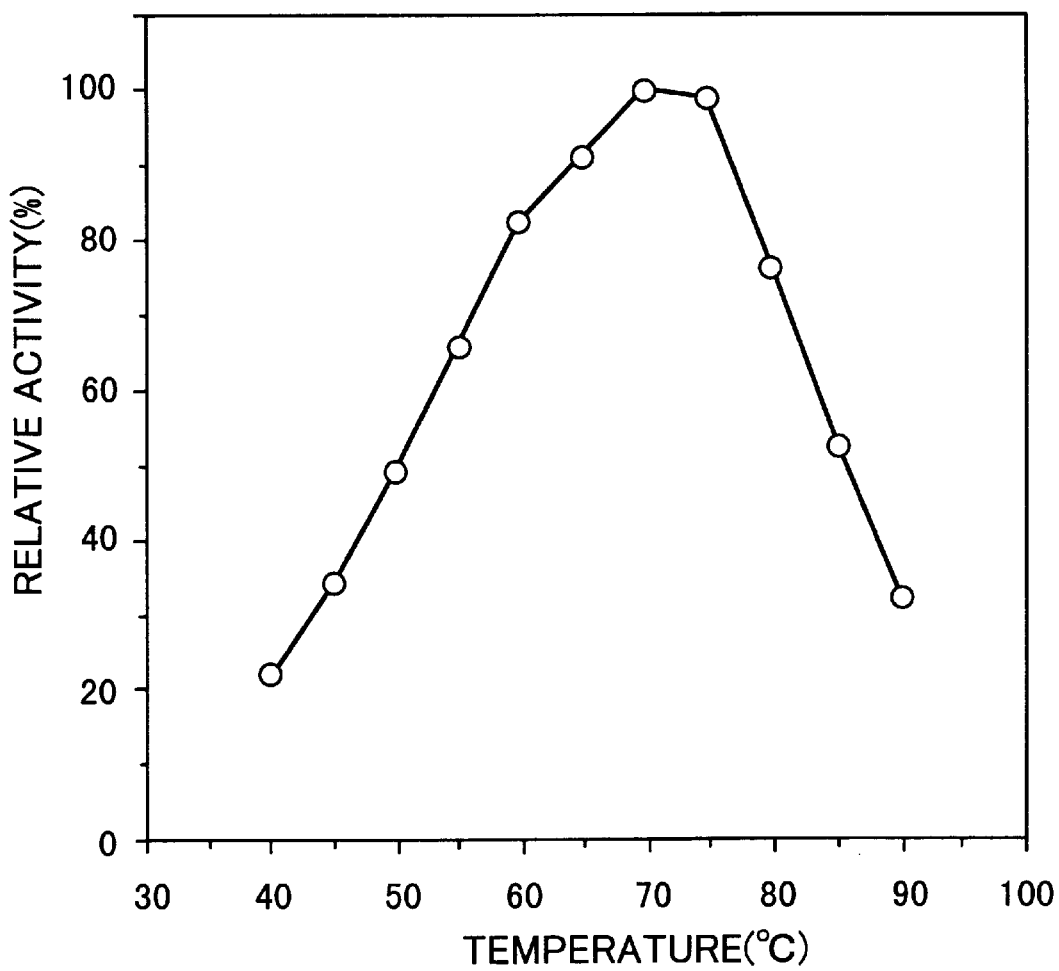
FIG. 3 is a graph showing the optimum temperature of the alkaline protease of the present invention.

The influence of the temperature on the activity of the enzyme was examined according to the foregoing activity-determination method. The activities of the enzyme relative to the maximum value which is assumed to be 100 are plotted on FIG. 3 as a function of temperature. The results shown in FIG. 3 indicate that the optimum temperature of the enzyme ranges from 70 to 75° C.

Figure 4:
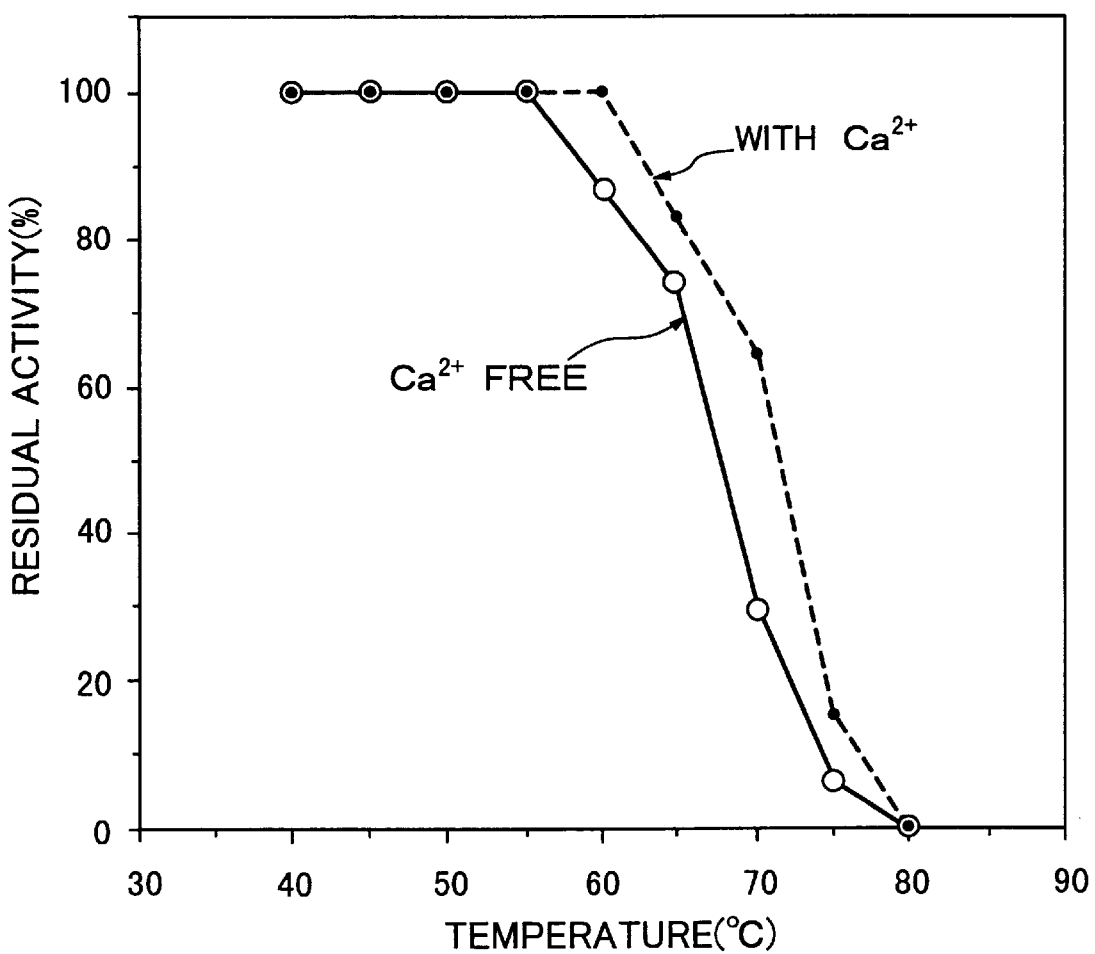
FIG. 4 is a graph showing the stable temperature range of the alkaline protease of the present invention.

Separately, the enzyme was added to a 50 mM Tris-HCl buffer (pH 7.0), followed by allowing the mixture to stand for 10 minutes while varying the temperature within the range of from 40 to 80° C. and determination of the remaining activity. The activity was determined at each temperature condition with or without addition of 5 mM calcium chloride. The results thus obtained are shown in FIG. 4. The data shown in FIG. 4 indicate that the enzyme is stable up to 55° C. in the absence of calcium ions and up to 60° C. in the presence of calcium ions. As a result, it was confirmed that the heat stability of the enzyme is improved by the addition of calcium ions.

(4) Molecular Weight:

The molecular weight of the enzyme was determined according to the SDS-PAGE method and was found to be about 56,000.

(5) Isoelectric Point:

The isoelectric point of the enzyme was determined by the isoelectric focusing method and was found to be in the range of from about 10 to 10.5.

(6) Specific Activity:

The specific activity of the enzyme was determined according to the foregoing activity-determination method. In this connection, the protein concentration was determined using the protein assay kit available from Japan Bio-Rad Laboratories Co., Tokyo and the enzyme used in the determination was a purified product to such an extent that it was electrophoretically uniform. As a result, it was found that the enzyme had a specific activity of 214,000 (U/mg protein) when using casein as a substrate and 52,700 (U/mg protein) when using keratin as a substrate and that the enzyme had very strong activity to hydrolyze proteins.

(7) Inhibition:

DFP (diisopropyl fluorophosphate), PMSF (phenyl methanesulfonyl fluoride), PCMB (p-chloromercuribenzoate), iodoacetic acid, EDTA (ethylene-diaminetetraacetic acid) and SDS (sodium dodecylsulfate), as general enzyme-inhibitors, were inspected for their inhibitory effect on the activity of the enzyme. More specifically, each inhibitor was dissolved in a 50 mM Tris-HCl buffer (pH 9.0) to a desired concentration, followed by addition of the enzyme and a treatment at 30° C. for 30 minutes. Then a predetermined quantity of a sample was taken from the treated solution to determine the residual activity of the sample according to the foregoing activity-determination method. The residual activity is expressed in terms of the value relative to that observed for a control free of any inhibitor, whose relative activity is assumed to be 100. The results thus obtained are summarized in the following Table 3.

TABLE 3

Influence of Various Kinds of Inhibitors

| Inhibitor | Concentration | Residual Activity |
|---|---|---|
| Control | None | 100 |
| DFP | 1 mM | 0 |
| PMSF | 1 mM | 0 |
| PCMB | 1 mM | 91 |
| Iodoacetic Acid | 1 mM | 96 |
| EDTA | 1 mM | 91 |
| SDS | 0.2% | 74 |

As seen from the results shown in Table 3, it is confirmed that the activity of the enzyme is inhibited by DFP and PMSF but is not inhibited by the other inhibitors. Accordingly, it could be concluded that the alkaline protease is a serine protease. In addition, the enzyme is slightly inhibited by SDS as a surfactant, but the enzyme still retains a sufficiently high activity and accordingly, it may be expected to use it in detergents or washing agents.

The enzyme showing the foregoing characteristic properties are compared with conventional alkaline proteases derived from known bacteria or actinomycete and the results obtained are summarized in the following Table 4.

TABLE 4

Comparison of Various Kinds of Alkaline Proteases

| Name of Enzyme or Strain | Present Invention TOTO-9305 | Alkaline Protease A* | AH 101 | Subtilisin B. subtilis |
|---|---|---|---|---|
| Molecular Weight | 56,000 | 50,000 | 29,000 | 22,700 |
| Isoelectric Point | 10.0–10.5 | 8.7 | 9.2 | 7.5–8.0 |
| Optimum pH: Casein | 11.0–11.5 | 12–13 | 12–13 | 10.5 |
| Keratin | >13 | | 11–12 | |
| Optimum Temp. (° C.) | 70–75 | 60 | 70 | 55 |
| Specific Activity: | | | | |
| (U/mg protein) Casein | 214,000 | 3,624 | 2,500 | 2,900 |
| Keratin | 52,700 | | 3,970 | |
| Reference | | 1, 2 | 3 | 3 |

| Name of Enzyme or Strain | Subtilisin BPN[1] | Subtilisin Carlsberg | Elastase Ya-B |
|---|---|---|---|
| Molecular Weight | 27,700 | 27,600 | 23,700 |
| Isoelectric Point | 7.8 | 9.8 | 10.6 |
| Optimum pH: Casein | 10.5 | 10.5 | 11.75 |
| Keratin | | | |

TABLE 4-continued

Comparison of Various Kinds of Alkaline Proteases

| Optimum Temp. (° C.) Specific Activity: | | 50 | 60 | |
|---|---|---|---|---|
| (U/mg protein) Casein | 2,200 | 6,500 | 12,400 | |
| Keratin | 436 | 888 | | |
| Reference | 3 | 3 | 3 | |

Each blank means that there is not any corresponding datum.
*An alkaline protease available from Seikagaku Kogyo K.K.
Reference 1: Aqr. Biol. Chem., 1974, 38, (1), pp. 37–44 2: Enzyme Data Sheet Library (Seikagaku Kogyo K.K.) 3: Bioscience and Industry, 1990, 48, (7), pp. 33–36

The results obtained in the comparison of the enzyme according to the invention with known ones listed in Table 4 clearly indicate that the enzyme of the present invention is a novel alkaline protease having a very high specific activity.

The present invention will hereinafter be described in more detail with reference to the following Examples, but the present invention is not restricted to these specific Examples.

EXAMPLE 1

Preparation of Crude Enzyme Powder

A precultured medium (50 ml) of Streptomyces sp. TOTO-9305 strain (shaking culture at 35° C. for 4 days) was inoculated into a small-sized jar fermentor which contained 4500 ml of a culture medium (pH 9.0) comprising 1.5% of soluble starch, 1.5% of skim milk, 0.3% of $K_2HCO_4$, 0.1% of yeast extract and 0.05% of $MgSO_4 \cdot 7H_2O$ and additionally containing 1.0% of $NaHCO_3$ separately sterilized and then cultivated at 35° C., for 4 days at a rate of aeration of 1 v/v/min and at a number of revolutions of 200 rpm. After completion of the cultivation, the culture medium was centrifuged at 8000 rpm for 10 minutes to remove the bacterial cell. Then the resulting supernatant was lyophilized to give 9 g of crude enzyme powder having an activity of 40 U/mg protein.

EXAMPLE 2

Preparation of Purified Enzyme

A precultured medium (50 ml) of Streptomyces sp. TOTO-9305 strain was inoculated into a small-sized jar fermentor containing 4500 ml of the same culture medium used in Example 1. The strain was then cultivated under the same conditions used in Example 1 and then the resulting culture medium was likewise centrifuged under the same conditions used in Example 1 to give 3800 ml of a culture supernatant. The supernatant was found to have a protease activity, as determined at pH 10.5, of 94.5 U/mg protein.

Then powdery ammonium sulfate was added to the supernatant up to 80% saturation, followed by allowing to stand, in the dark, at 5° C. over a whole day and night and centrifugation at 8000 rpm to thus recover the precipitates. The precipitates were dissolved in a 10 mM phosphate buffer (pH 7.0) and then dialyzed against the same buffer using a cellulose tube. After completion of the dialysis, the internal solution (dialyzed solution) was passed through a column packed with CM-Toyopearl 650M which had been equilibrated with a 10 mM MOPS buffer (pH 7.5) containing 1 mM $CaCl_2$ added thereto to thus adsorb the enzyme thereon and then it was eluted with NaCl solution having a concentration gradient ranging from 0 to 0.5M. The resulting active fractions were dialyzed, then passed through a column packed with DEAE-Toyopearl 650M which had been equilibrated with a 10 mM Tris-HCl buffer (pH 9.0) containing 1 mM $CaCl_2$ added thereto to thus adsorb the impurity proteins thereon. An alkaline protease (34 ml) having an activity of 1920 U/ml was obtained through a series of the foregoing purification procedures. The resulting fraction showed a single band and a single peak in the SDS-electrophoresis and gel filtration analyses respectively and this clearly indicates that the enzyme is a uniform enzyme protein.

What is claimed is:

1. An alkaline protease which is produced by Streptomyces Sp. TOTO-9305 strain which has been accorded Accession No. FERM P-13640 having the following physical and chemical properties:

(a) it possesses non-specific endoproteolytic activity;

(b) the optimum pH of the enzyme ranges from 11.0 to 11.5 when using casein as a substrate;

(c) it is stable within the pH range of from 1.5 to 12.0 when it is treated at 30° C. for 24 hours;

(d) the optimum operating temperature of the enzyme ranges from 70 to 75° C.;

(e) the enzyme is stable up to 55° C. in the absence of calcium ions and up to 60° C. in the presence of calcium ions, when it is treated at pH 7.0 for 10 minutes;

(f) the enzyme has a molecular weight of about 56,000 (as determined by the SDS-PAGE method);

(g) the enzyme has an isoelectric point ranging from about 10 to 10.5 (as determined by the isoelectric focusing method);

(h) the enzyme has a specific activity of 214,000 (U/mg protein) when using casein as a substrate and 52,700 (U/mg protein) when using keratin as a substrate; and (i) the activity of the enzyme is not inhibited by PCMB (p-chloromercuribenzoate), iodoacetic acid and EDTA (ethylenediaminetetraacetic acid), but is inhibited by DFP (diisopropylfluorophosphate) and PMSF (phenyl methanesulfonyl fluoride).

2. A protein decomposing agent comprising the protease of claim 1.

3. A cleansing agent comprising the protease of claim 1.

4. A detergent comprising the protease of claim 1.

5. A hair decomposing agent comprising the protease of claim 1.

6. An agent for inhibiting blockage of drains caused by the build-up of proteins comprising the protease of claim 1.

7. A method for producing the alkaline protease according to claim 1 comprising the steps of cultivating Streptomyces Sp. TOTO-9305, which strain has been accorded Accession No. FERM P-13640 and isolating said alkaline protease from the culture medium obtained in said cultivation step.

8. The method of claim 7 wherein the microorganism is cultivated under an alkaline pH condition ranging from 8.0 to 13.0.

9. A method for decomposing insoluble protein which comprises the step of applying the protease of claim 1 to an insoluble protein or material containing the same.

10. The method of claim 9 wherein the insoluble protein is keratin.

11. The method of claim 9 wherein the material is hair.

* * * * *